United States Patent [19]

Sinou

[11] Patent Number: 5,135,900

[45] Date of Patent: Aug. 4, 1992

[54] PALLADIUM-BASED CATALYST AND ITS USE

[75] Inventor: Denis Sinou, Bonhomme, France

[73] Assignee: Rhone-Poulenc Sante, Cedex, France

[21] Appl. No.: 540,603

[22] Filed: Jun. 20, 1990

[30] Foreign Application Priority Data

Jun. 22, 1989 [FR] France ................... 89 08318

[51] Int. Cl.⁵ ............................................. B01J 31/24
[52] U.S. Cl. ................................... 502/155; 502/152; 502/162; 502/167
[58] Field of Search ................. 502/162, 167, 155, 152

[56] References Cited

U.S. PATENT DOCUMENTS

| | | | |
|---|---|---|---|
| 4,142,060 | 2/1979 | Kuntz | 568/840 |
| 4,356,333 | 10/1982 | Yoshimura et al. | 502/162 |
| 4,399,312 | 8/1983 | Russell et al. | 502/162 |
| 4,654,176 | 3/1987 | Dang et al. | 260/505 R |

FOREIGN PATENT DOCUMENTS 0287066 10/1988 European Pat. Off. .
2366237 4/1978 France .

OTHER PUBLICATIONS

Tetrahedron, J. Tsuji, vol. 42, No. 16, pp. 4361–4401, 1986.
Chemistry Letters, J. Kiji et al., pp. 957–960, 1988.

*Primary Examiner*—Patrick P. Garvin
*Assistant Examiner*—Brent M. Peebles
*Attorney, Agent, or Firm*—Finnegan, Henderson, Farabow, Garrett and Dunner

[57] ABSTRACT

A catalyst system comprising an aqueous solution of a derivative of palladium and of a water-soluble ligand associated with a nitrile, and its use, for example, for effecting allyl substitution reactions in a two-phase system with easy recycling of the catalyst after phase separation.

11 Claims, No Drawings

PALLADIUM-BASED CATALYST AND ITS USE

BACKGROUND OF THE INVENTION

The present invention is directed to a palladium-based catalyst system comprising an aqueous solution of a derivative of palladium and of a water-soluble ligand associated with a nitrile, and the use of the palladium-based catalyst system in organic chemistry in reactions employing palladium-based catalysts, and more particularly, in nucleophilic substitution reactions.

Nucleophilic reactants have been reacted with allyl derivatives such as cinnamyl acetate or with geranyl acetate in the presence of catalysts selected from palladium complexes optionally in the presence of ligands such as triphenylphosphine [J. Tsuji, Tetrahedron, 42, 4361–4401 (1986)]. Reactions of telomerization of dienes with compounds containing mobile hydrogen (FR 2,366,237, EP 287,066) or carbonylation reactions [J. Kiji et al., Chem. Letters, 957–960 (1988)] using catalysts consisting of a transition metal associated with a soluble phosphine have been performed. However, the use of these processes does not make it possible to separate the reaction products easily from the catalyst, which is soluble in the organic solvents employed. Accordingly, the separation of the reaction products is difficult, and furthermore, the catalyst cannot be recovered easily and recycled.

It has now been found according to the catalyst system of the present invention that a catalyst comprising an aqueous solution of a palladium derivative and of a water-soluble ligand, associated with a nitrile, can be easily separated from the reaction products and easily recycled.

SUMMARY OF THE INVENTION

Accordingly, this invention is directed to a palladium-based catalyst system which comprises an aqueous solution of a derivative of palladium and of a water-soluble ligand associated with a nitrile. Furthermore, this invention is also directed to the use of the catalyst system for effecting nucleophilic substitutions, comprising the steps of reacting a nucleophile Nu selected, for example, from compounds containing an active methylene group, azides, cyanides, phenates, thiolates, sulphinates, primary or secondary amines, hydroxylamines and formates; with a product of the formula (I):

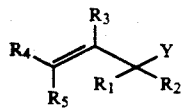

in which

R$_1$, R$_2$, R$_3$, R$_4$ and R$_5$, which are identical or different, are a hydrogen atom, an optionally functionalized aliphatic hydrocarbon radical, an aromatic radical, a cyano radical or an alkanoyloxy radical whose alkanoyl part contains 1 to 4 carbon atoms, and wherein:

R$_1$ and R$_5$ can independently together form an alkylene radical containing 2 or 3 carbon atoms, and R$_3$ and R$_4$ can independently together form a bond, and —C(R$_1$R$_2$)Y can independently form the chain sequence of the formula (IV)

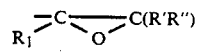

in which

R' and R", which are identical or different, are a hydrogen atom or an alkyl radical containing 1 to 4 carbon atoms, and Y is a halogen atom selected from the group consisting of chlorine, bromine, and iodine or a radical —OR, —SR, —O—CO—OR, —O—CO—N(R)$_2$, —O—PO(OR)$_2$, —NR$_2$, —NO$_2$, —SO$_2$R, —N(R$_3$)X, S(R)$_2$X or —O—C(R)=N—R, wherein R is an alkyl radical containing 1 to 4 carbon atoms or an aryl radical and X is an anion, in the presence of a sufficient quantity of a catalyst system according to the catalyst system of this invention preferably at a temperature below 200° C.

Subsequently, it is preferable to separate the reaction product by phase separation and preferably recover the aqueous catalyst solution, which can be preferably recycled.

DETAILED DESCRIPTION OF THE INVENTION

The palladium compound which can be employed for preparing the catalyst system must be soluble in water or at least be capable of dissolving in water by a coordination reaction with the water-soluble ligand.

The palladium compounds may be selected from derivatives of palladium in an oxidation state of zero or in an oxidation state other than zero.

The palladium compounds in which the palladium is in an oxidation state other than zero are selected from, for example, palladium salts of organic acids, such as a palladium acetate and palladium citrate, and palladium carbonate, borate, bromide, chloride, iodide, hydroxide, nitrate, sulphate, alkyl- or arylsulphonate and acetylacetonate, bisbenzonitrile-palladium chloride, potassium tetrachloropalladate, π-allylpalladium chloride and π-allylpalladium acetate.

The palladium compounds in which the palladium is in the oxidation state of zero are selected from, for example, tetrakistriphenylphosphinepalladium(0), bis-dibenzylideneacetonepalladium(0) and bis-1,5-cyclooctadienepalladium(0).

In general, a quantity of palladium or of palladium compound is employed such that the number of gram-atoms of elemental palladium per liter of aqueous catalyst solution is preferably from $10^{-4}$ to 1 and, more preferably, from $10^{-3}$ to 0.5.

The water-soluble ligands may be selected, for example, from the water-soluble phosphines which are described in U.S. Pat. No. 4,142,060 and in U.S. Pat. No. 4,654,176. The teachings of water-soluble phosphines in both patents are herein incorporated by reference.

The water-soluble ligand can be selected from, for example, sulphonated phosphines and diphosphines. Tri-meta-sulphotriphenylphosphine (TPPTS) and tri-meta-sulphotriphenylphosphine in the form of sodium salt (NaTPPTS) are preferred water-soluble phosphines.

In general, a quantity of ligand is employed such that the number of gram-atoms of ligand in relation to one gram-atom of palladium is preferably from 1 to 200 and, more preferably, from 3 to 100.

The nitrile which is associated with the aqueous solution of the palladium compound is preferably benzonitrile or butyronitrile.

In general, the volume of nitrile employed is preferably from 0.01 to 100 times the volume of the aqueous solution of the palladium compound, and more preferably from 0.1 to 10 times.

To make use of the catalyst system according to a preferred embodiment of the invention, it may be advantageous to add the aqueous solution of the palladium compound to the solution of the reactants which are solubilised in the nitrile for the nucleophilic substitution in the nitrile.

The catalyst system according to the present invention can be employed for carrying out, in a two-phase medium, reactions which make use of a palladium-based catalyst and are usually carried out in a homogeneous organic medium.

More particularly, the catalyst system according to the invention can be employed for effecting nucleophilic substitutions by the action of a nucleophilic reactant Nu on a product of the formula (I):
in which $R_1$, $R_2$, $R_3$, $R_4$, and $R_5$, which are identical or different, are a hydrogen atom or an optionally functionalized aliphatic hydrocarbon radical, an aromatic radical, a cyano radical or an alkanoyloxy radical whose alkanoyl part contains 1 to 4 carbon atoms, and wherein $R_1$ and $R_5$ can independently together form an alkylene radical containing 2 or 3 carbon atoms, and $R_3$ and $R_4$ can independently together form a bond, and $-C(R_1R_2)Y$ can independently form the chain sequence of the formula (IV):
in which R' and R'', which are identical or different, are a hydrogen atom or an alkyl radical containing 1 to 4 carbon atoms, and Y is a halogen atom selected from the group consisting of chlorine, bromine, and iodine or a radical $-OR$, $-SR$, $-O-CO-OR$, $-O-CO-N(R)_2$, $-O-PO(OR)_2$, $-NR_2$, $-NO_2$, $-SO_2R$, $-N(R_3)X$, $-S(R)_2X$, or $-O-C(R)=N-R$, wherein R is an alkyl radical containing 1 to 4 carbon atoms or an aryl radical, and X is an anion, In this invention, an aliphatic hydrocarbon radical is an alkyl radical containing 1 to 20 carbon atoms or an alkenyl radical containing 2 to 20 carbon atoms and optionally more than one double bond, conjugated or otherwise.

The nucleophilic reactant which can react with the product of general formula (I) is generally selected from compounds which are capable of generating an anion.

Preferably, the nucleophile Nu, $Nu_1$ and $Nu_2$ is selected from compounds containing an active methylene group, for example, methyl or ethyl acetylacetate; azides, for example, sodium azide; cyanides, for example, sodium cyanide; phenates, for example, sodium phenate; thiolates; sulphinates; primary or secondary amines; hydroxylamines; and formates.

When a nucleophile Nu is reacted with a product of formula (I) in which Y is defined as above in formula (I) and $R_1$, $R_2$, $R_3$, $R_4$ and $R_5$, which are identical or different, are a hydrogen atom or an aliphatic hydrocarbon radical or an aromatic radical, it being possible for the radicals $R_1$ and $R_5$ to form an alkylene radical containing 2 or 3 carbon atoms, products of the formula (V) and/or (VI):

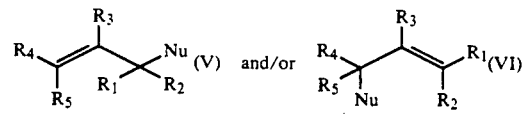

are obtained.

When a nucleophile Nu', selected from hydrogen, an alcohol and a primary or secondary amine is reacted with a product of formula (I) in the presence of carbon monoxide, products of the formula (VII and/or VIII):

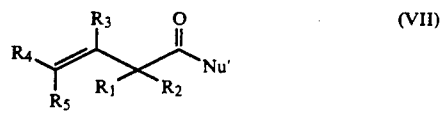

and/or

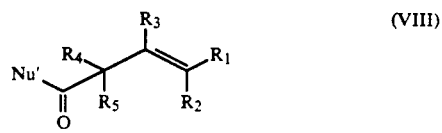

are obtained.

When a nucleophile $Nu_1$ is reacted with a product of formula (II):

in which Y is defined as above in formula (I) and $R_1$, $R_2$ and $R_3$, which are identical or different, are a hydrogen atom, an aliphatic hydrocarbon radical or an aromatic radical, a product of the formula (IX):

is obtained, which can be reacted with an excess of the same nucleophile or a different nucleophile $Nu_2$ to obtain a product of the formula (X):

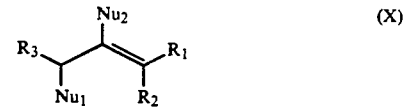

When a nucleophile Nu is reacted with a product of formula (III):

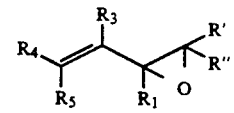

in which $R_1$, $R_3$, $R_4$ and $R_5$, which are identical or different, are a hydrogen atom or an aliphatic hydrocarbon radical or an aromatic radical and R' and R'', which are identical or different, are a hydrogen atom or an alkyl radical containing from 1 to 4 carbon atoms, products of the formula (XI and/or XII):

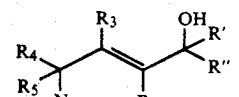 (XI)

and/or

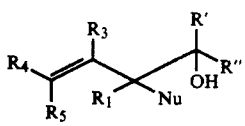 (XII)

are obtained.

The process is generally carried out by adding the aqueous catalyst solution to the solution of the product of formula (I), (II) or (III) and of the nucleophile Nu in the nitrile, and then heating the stirred mixture to a temperature below 200° C.

The aqueous catalyst solution can be prepared in situ by mixing the palladium derivative and the ligand in water. The operation can be carried out under inert atmosphere, for example, in nitrogen or argon.

The reaction mixture may be heated before or after the introduction of the product of formula (I), (II) or (III), which can itself be introduced before or after the nucleophile Nu, or simultaneously.

The molecular ratio of the nucleophile Nu to the product of formula (I), (II) or (III) is not critical. However, it is particularly advantageous to operate in the presence of a slight molar excess of the nucleophile Nu.

The process is preferably carried out at a temperature below 200° C. and more preferably from 20° to 100° C.

At the end of reaction and after cooling to a temperature in the region of 20° C., the reaction mixture, consisting of two immiscible phases, is separated, for example, by density separation, into an aqueous phase containing the catalyst system and an organic phase containing the reaction product.

The aqueous phase can be employed for catalyzing a new reaction of a product of formula (I), (II) or (III) with the nucleophile Nu.

The products obtained according to the process of the present invention are particularly useful as organic synthesis intermediates for the preparation of perfumes or of vitamins. For example, the product of condensation of ethyl geranyl carbonate with methyl acetylacetate makes it possible to prepare geranyl acetone according to Tsuji et al., J. Org. Chem. 50, 1523 (1985). The products obtained according to the process of the present invention can also be employed for preparing vitamin A according to the process described in French Patent Fr 2,589,862. Other applications are described, for example, in the paper by J. Tsuji, J. Organometal. Chem., 300, 281–305 (1986).

The following examples, given without any limitation being implied, show how the invention can be put into practice.

EXAMPLE 1

Palladium acetate [Pd(OAc)$_2$] (33.6 mg, i.e. 0.15 mg-at. of palladium) and NaTPPTS (735 mg, i.e. 1.2 mg-at. of P$^{3+}$) were dissolved in degassed water (5 cc) under an argon atmosphere. This solution was injected into a reactor containing ethyl cinnamyl carbonate (618 mg, 3 mmol) and ethyl acetylacetate (585 mg, 4.5 mmol) in benzonitrile (5 cc). The mixture was stirred at 50° C. for 18 hours. After cooling, the reaction mixture consisted of a light orange-colored aqueous phase and of a light yellow organic phase.

The organic phase was separated off and concentrated under reduced pressure. A dark yellow oil (450 mg) was thus obtained, which was purified by chromatography on a silica 60 column, eluted with a hexane-ethyl acetate mixture.

Ethyl 5-phenyl-2-acetyl-4-pentenoate (440 mg) was thus obtained, whose structure was confirmed by the infrared spectrum, the proton and $^{13}$C nuclear magnetic resonance spectrum and elemental analysis.

The degree of conversion of ethyl cinnamyl carbonate was 94% and the selectivity for the monosubstitution product was close to 100%.

Ethyl cinnamyl carbonate (618 mg, 3 mmol) and ethyl acetylacetate (585 mg, 4.5 mmol) in benzonitrile (5 cc) were added into a reactor containing the aqueous phase obtained previously. The mixture was stirred at 50° C. for 18 hours. By treating the reaction mixture in the same way as before, ethyl 5-phenyl-2-acetyl-4-pentenoate (413 mg) was obtained.

The degree of conversion of ethyl cinnamyl carbonate was 93% and the selectivity for the monosubstitution product was 100%.

By carrying out a second recycling under the conditions described above the monosubstitution product was obtained with a selectivity of 100%, the degree of conversion of ethyl cinnamyl carbonate was close to 100%.

COMPARATIVE EXAMPLES

The results obtained by using the catalyst system under the conditions described above in the absence of one of the constituents were collated in Table I shown below.

TABLE I

| Catalyst | Ligand | Solvent | Degree of conversion (%) |
|---|---|---|---|
| Pd(dba)$_2$ | TPPTS | Isopropyl ether | 80* |
| Pd(dba)$_2$ | TPPTS | n-Butyl ether | 0* |
| — | — | Benzonitrile | 0 |
| Pd(dba)$_2$ | — | Benzonitrile | 0 |
| — | TPPTS | Benzonitrile | 0 |

*Appearance of a metallic deposit of palladium

EXAMPLE 2

Bisdibenzylideneacetonepalladium(0) [Pd(dba)$_2$)] (28 mg, i.e. 0.05 mg-at. of palladium) and NaTPPTS (172 mg, i.e. 0.28 mg-at. of P$^{3+}$) were dissolved in degassed water (3 cc) under an argon atmosphere. This solution was injected into a reactor containing ethyl cinnamyl carbonate (211 mg, 1 mmol) and ethyl acetylacetate (200 mg, 1.54 mmol) in benzonitrile (3 cc). The mixture was stirred at 50° C. for 18 hours. The reaction mixture was treated under the conditions of Example 1.

Ethyl 5-phenyl-2-acetyl-4E-pentenoate (176 mg) was thus obtained. E in the above product denotes the trans isomer.

The degree of conversion of ethyl cinnamyl carbonate was 100%.

The selectivity for the monosubstitution product was 100%.

Ethyl cinnamyl carbonate (208 mg, 1 mmol) and ethyl acetylacetate (204 mg, 1.57 mmol) were added to the aqueous phase obtained previously. The mixture was stirred at 50° C. for 18 hours.

The reaction mixture was treated under the conditions described in Example 1.

Ethyl 5-phenyl-2-acetyl-4E-pentenoate (130 mg) was thus obtained.

The degree of conversion of ethyl cinnamyl carbonate was 60%.

The selectivity for the monosubstitution product was 100%.

The results obtained during the following recycling operations were collated in Table II shown below.

TABLE II

| Recycling | Degree of conversion (%)* | Yield (%) based on the carbonate consumed** |
|---|---|---|
| No. 2 | 75 | 62 |
| No. 3 | 64 | 58 |
| No. 4 | 54 | 45 |

*Determination from the nuclear magnetic resonance spectrum
**Determination after separation on a column

EXAMPLE 3

[Pd(OAc)$_2$] (27 mg, i.e. is 0.12 mg-at. of palladium), NaTPPTS (290 mg. i.e. is 0.50 mg-at. of P$^{3+}$) and sodium azide (695 mg) were dissolved under an argon atmosphere. This solution was injected into a reactor containing cinnamyl acetate (455 mg, 2.6 mmol) in benzonitrile (3 cc). The mixture was stirred at 50° C. for 3 hours. After cooling, the reaction mixture was treated under the conditions of Example 1.

The organic phase, separated off and concentrated under reduced pressure, yielded 1-azido-3-phenyl-2-propene (330 mg) whose structure was confirmed by the infrared spectrum, the proton nuclear magnetic resonance spectrum and elemental analysis.

The degree of conversion of cinnamyl acetate was 100% and the selectivity for azide was 100%.

Cinnamyl acetate (445 mg, 2.5 mol) in benzonitrile (3 cc) was added into the reactor containing the aqueous phase. The mixture was stirred at 50° C. for 3 hours.

The reaction mixture was treated as before. 1-Azido-3-phenyl-2-propene (400 mg) was thus obtained.

The degree of conversion of the cinnamyl acetate was close to 100% and the selectivity for azide was close to 100%.

EXAMPLE 4

[Pd(OAc)$_2$] (24 mg, i.e. 0.1 mg-at. of palladium) and NaTPPTS (422 mg, i.e. 0.7 mg-at. of P$^{3+}$) were dissolved in degassed water (5 cc) under an argon atmosphere. This solution was injected into a reactor containing ethyl geranyl carbonate (467 mg) and ethyl acetylacetate (556 mg, 3.6 mmol) in benzonitrile (5 cc). The mixture was stirred at 50° C. for 24 hours. After cooling, the reaction mixture was treated under the conditions of Example 1.

The organic phase, separated off and concentrated under reduced pressure, yielded a dark yellow oil (440 mg) whose analysis by proton nuclear magnetic resonance and by vapor phase chromatography showed that it consisted of:

55% of 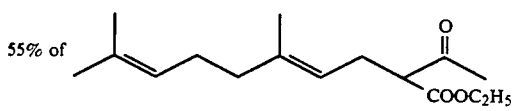

37% of 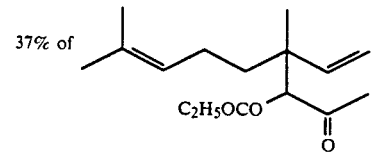

8% of 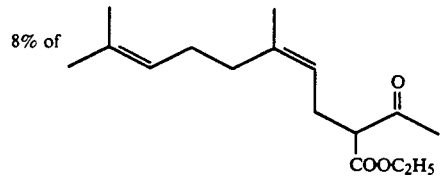

E and Z above refer to the trans and cis isomers, respectively. The degree of conversion of ethyl geranyl carbonate was 100%.

EXAMPLE 5

[Pd(OAc)$_2$] (31 mg, i.e. 0.14 mg-at. of palladium) and NaTPPTS (582 mg, 0.95 mg-at. of P$^{3+}$) were dissolved in degassed water (5 cc) under an argon atmosphere. This solution was injected into a reactor containing ethyl cinnamyl carbonate (427 mg, 2.0 mmol) and morpholine (274 mg, 2.7 mmol) in benzonitrile (5 cc). The mixture was stirred at 50° C. for 18 hours. The reaction mixture was treated under the conditions of Example 1.

The organic phase, separated off and concentrated under reduced pressure, yielded an oil (350 mg) whose analysis by nuclear magnetic resonance showed it to consist of 1-(3-phenyl-2-propen-1-yl)morpholine.

The degree of conversion of ethyl cinnamyl carbonate was 100% and the selectivity for the monosubstitution product was 100%.

Ethyl cinnamyl carbonate (420 mg, 2 mmol) and morpholine (260 mg, 3 mmol) in benzonitrile (5 cc) were added into the reactor containing the aqueous phase. The mixture was stirred at 50° C. for 12 hours.

The reaction mixture was treated in the same way as above. 1-(3-Phenyl-2-propen-1-yl)morpholine (345 mg) was obtained.

The degree of conversion of ethyl cinnamyl carbonate was 100%.

EXAMPLE 6

[Pd(OAc)$_2$] (24 mg, i.e. 0.1 mg-at. of palladium), NaTPPTS (290 mg, i.e. 0.50 mg-at. of P$^{3+}$) and sodim sulphinate (1340 mg, 7.5 mmol) were dissolved in degassed water (5 cc) under an argon atmosphere. This solution was injected into a reactor containing ethyl cinnamyl carbonate (502 mg, 2.5 mmol) in benzonitrile (3 cc). The mixture was stirred at 50° C. for 5 hours. After cooling, the mixture was treated under the conditions of Example 1.

The organic phase, separated off and concentrated under reduced pressure, yielded p-tolyl 3-phenyl-2-propene sulphone (460 mg; yield=95%) whose structure was confirmed by nuclear magnetic resonance and elemental analysis.

Ethyl cinnamyl carbonate (500 mg, 2.5 mmol) in benzonitrile (5 cc) was added into the reactor containing the aqueous phase. The mixture was stirred at 50° C. for 12 hours. After the same treatment as before, p-tolyl 3-phenyl-2-propene sulphone (635 mg; 95% yield) was obtained.

EXAMPLE 7

[Pd(OAc)$_2$] (27 mg, i.e. 0.12 mg-at. of palladium) and NaTPPTS (290 mg, i.e. 0.5 mg-at. of P$^{3+}$) were dissolved in degassed water (3 cc) under an argon atmosphere. This solution was injected into a reactor containing 3,4-epoxy-1-butene (210 mg, 3 mmol) and ethyl acetylacetate (590 mg, 4.5 mmol) in acetonitrile (3 cc). The mixture was stirred at 50° C. for 24 hours. After cooling, the organic phase was extracted with ethyl acetate (2×5 cc). After concentration under reduced pressure and chromatography on a silica column, (E,Z) ethyl 6-hydroxy-2-acetyl-3-hexanoate (480 mg; yield=80%) was obtained, whose structure was confirmed by $^1$H and $^{13}$C nuclear magnetic resonance and elemental analysis.

The degree of conversion of the epoxide was 100% and the selectivity for the substitution product was close to 100%, with an E-Z ratio of 85/15.

3,4-epoxy-1-butene (200 mg, 38 mmol) and ethyl acetylacetate (580 mg, 4.5 mmol) in acetonitrile (5 cc) were added to the aqueous phase obtained previously. The mixture was stirred at 50° C. for 20 hours.

After cooling, extracting with ethyl acetate (3×3 cc) and evaporating off the solvent, (E/Z) ethyl 6-hydroxy-2-acetyl-3-hexenoate (487 mg; 87% yield) was obtained after purification on a silica column. The degree of conversion and the selectivity were 100%.

EXAMPLE 8

Palladium acetate [Pd(OAc)$_2$] (33.5 mg, i.e. 0.15 mg-at. of palladium) and NaTPPTS (740 mg, i.e. 1.2 mg-at. of P$^{3+}$) were dissolved in degassed water (3 cc) under an argon atmosphere. This solution was injected into a reactor containing ethyl cinnamyl carbonate (620 mg, 3 mmol) and 2,2-dimethyl-1,3-dioxan-4,6-dione (720 mg, 5 mmol) in benzonitrile (5 cc). The mixture was stirred at 50° C. for 20 hours. After cooling, the organic phase was separated off and concentrated under reduced pressure; the oil obtained was purified by chromatography on a silica column to give (E) 5-(3-phenyl-2-propene)-2,2-dimethyl-1,3-dioxan-4,6-dione (505 mg; 65% yield), whose structure was confirmed by nuclear magnetic resonance and elemental analysis.

What is claimed is:

1. A palladium-based catalyst system which comprises an aqueous solution of a palladium compound and of a water-soluble ligand selected from sulphonated phosphines and diphosphines, said aqueous solution being associated with a nitrile solvent, wherein the volume of the nitrile solvent is 0.1 to 10 times the volume of the aqueous solution of the palladium compound.

2. The catalyst system according to claim 1, wherein the palladium compound is selected from compounds of palladium in an oxidation state of zero.

3. The catalyst system according to claim 2, wherein the palladium compound is selected from palladium salts of organic acids, palladium carbonate, borate, bromide, chloride, iodide, hydroxide, nitrate, sulphate, alkyl- or arylsulphonate and acetylacetonate, bisbenzonitrile-palladium chloride, potassium tetrachloropalladate, π-allylpalladium chloride, π-allylpalladium acetate, tetrakistriphenylphosphinepalladium(0), bisdibenzylidene-acetonepalladium(0) and bis-1,5-cyclooctadienepalladium(0).

4. The catalyst system according to claim 1, wherein the ligand is selected from tri-meta-sulphotriphenylphosphine and tri-meta-sulphotriphenylphosphine in the form of sodium salt.

5. The catalyst system according to claim 1, wherein the nitrile solvent is selected from benzonitrile and butyronitrile.

6. The catalyst system according to claim 1, wherein the aqueous catalyst solution contains from $10^{-4}$ to 1 gram-atom of palladium per liter of aqueous catalyst solution.

7. The catalyst system according to claim 1, wherein the aqueous catalyst solution contains from 1 to 200 moles of ligand per gram-atom of palladium.

8. The catalyst system according to claim 4, wherein the aqueous catalyst solution contains from 1 to 200 gram-atoms of trivalent phosphorous per gram-atom of palladium.

9. The catalyst system according to claim 3, wherein the palladium salt of an organic acid is selected from palladium acetate and palladium citrate.

10. The catalyst system according to claim 1, wherein the palladium compound is selected from compound of palladium in an oxidation state other than zero.

11. The catalyst system according to claim 10, wherein the palladium compound is selected from palladium salts of organic acids, palladium carbonate, borate, bromide, chloride, iodide, hydroxide, nitrate, sulphate, alkyl- or arylsulphonate and acetylacetaonate, bisbenzonitrile-palladium chloride, potassium tetrachloropalladate, π-allylpalladium chloride, π-allylpalladium acetate, tetrakistriphenylphosphinepalladium(0), bisdibenzylidene-acetonepalladium(0) and bis-1,5-cyclooctadienepalladium (0).

* * * * *

UNITED STATES PATENT AND TRADEMARK OFFICE
CERTIFICATE OF CORRECTION

PATENT NO. : 5,135,900
DATED : August 04, 1992
INVENTOR(S) : Denis Sinou

It is certified that error appears in the above-identified patent and that said Letters Patent is hereby corrected as shown below:

Claim 10, column 10, line 40, change "compound" (second occurrence) to --compounds--.

Claim 11, column 10, line 46, change "acetylacetaonate" to --acetylacetonate--.

Signed and Sealed this

Twenty-sixth Day of October, 1993

Attest:

BRUCE LEHMAN

Attesting Officer

Commissioner of Patents and Trademarks